US008975901B2

(12) United States Patent
Birecki et al.

(10) Patent No.: US 8,975,901 B2
(45) Date of Patent: Mar. 10, 2015

(54) MEASUREMENT DEVICE AND METHOD THEREOF

(75) Inventors: Henryk Birecki, Palo Alto, CA (US); Omer Gila, Cupertino, CA (US); Michael H Lee, San Jose, CA (US); William D Holland, Palo Alto, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 469 days.

(21) Appl. No.: 13/280,045

(22) Filed: Oct. 24, 2011

(65) Prior Publication Data

US 2013/0099798 A1   Apr. 25, 2013

(51) Int. Cl.
*G01R 27/28* (2006.01)
*G01N 27/07* (2006.01)
*G01R 27/22* (2006.01)

(52) U.S. Cl.
CPC ............... *G01N 27/07* (2013.01); *G01R 27/22* (2013.01)
USPC ........... 324/649; 324/436; 324/441; 324/444; 324/446; 324/447; 324/448; 324/449; 324/450; 324/691; 324/692; 324/693; 324/694; 324/695; 324/696; 324/697; 324/698; 324/701; 324/707; 324/710; 324/712; 324/713; 324/721; 324/722

(58) Field of Classification Search
CPC ....... G01R 27/22; G01N 27/06; G01N 27/07; G01N 27/08; G01N 33/2888; G03G 15/105
USPC ......... 324/439, 441, 444, 446–450, 691–698, 324/701, 707, 710, 712–713, 721, 722, 649
See application file for complete search history.

(56) References Cited

U.S. PATENT DOCUMENTS

| | | | | |
|---|---|---|---|---|
| 4,011,501 A * | 3/1977 | Peterson et al. | ............... | 324/694 |
| 4,213,114 A * | 7/1980 | Cochard | ........................ | 340/945 |
| 4,686,857 A * | 8/1987 | Kato | ........................... | 73/304 R |
| 4,806,955 A * | 2/1989 | Koto et al. | ....................... | 347/30 |
| 6,077,479 A * | 6/2000 | Milde et al. | ...................... | 422/23 |
| 6,222,371 B1 * | 4/2001 | Snyder | ........................... | 324/439 |
| 6,330,406 B1 * | 12/2001 | Yamaguchi | ..................... | 399/58 |
| 6,470,744 B1 * | 10/2002 | Usui et al. | .................... | 73/290 R |

(Continued)

FOREIGN PATENT DOCUMENTS

| | | |
|---|---|---|
| WO | WO-2009145788 | 12/2009 |
| WO | WO-2010056243 | 5/2010 |

OTHER PUBLICATIONS

Hanna Instruments, "Portable Microprocessor Printing and Logging Multi-range Conductivity Meters" http://www.hannainst.com/manuals/manHI_933300_933301.pdf.

*Primary Examiner* — Patrick Assouad
*Assistant Examiner* — Sean Curtis (57) ABSTRACT

Measurement devices, systems, and methods to measure a high field conductivity of a fluid are provided herein. The measurement device includes a fluid cell, a pair of electrodes, a voltage switch, and a measurement unit. The fluid cell is on an inclined plane to receive the fluid. The pair of electrodes are connected to the fluid cell. The pair of electrodes are spaced apart from one another to receive the fluid therebetween and positioned parallel to one another to pass an electrical current therethrough. The power unit provides a high voltage power supply to one electrode of the pair of electrodes. The measurement unit measures the electrical current that passes between the pair of electrodes through the fluid.

20 Claims, 11 Drawing Sheets

(56) References Cited

U.S. PATENT DOCUMENTS

| | | |
|---|---|---|
| 6,598,963 B1* | 7/2003 | Yamamoto et al. ............ 347/85 |
| 7,088,932 B2* | 8/2006 | Chou et al. .................... 399/57 |
| 7,675,298 B2* | 3/2010 | Forgacs ........................ 324/713 |
| 2002/0167571 A1* | 11/2002 | Hayashi et al. ............... 347/85 |
| 2003/0001934 A1* | 1/2003 | Kitabatake et al. ............ 347/86 |
| 2003/0202822 A1* | 10/2003 | Viturro et al. ................ 399/223 |
| 2005/0210979 A1* | 9/2005 | Urano et al. ................ 73/514.09 |
| 2007/0284250 A1* | 12/2007 | Magnant et al. ............. 204/459 |
| 2009/0033693 A1* | 2/2009 | Tanaka ............................. 347/7 |
| 2010/0299068 A1* | 11/2010 | Mason et al. ..................... 702/7 |
| 2010/0321046 A1* | 12/2010 | Randall et al. ............... 324/696 |

* cited by examiner

| Settings | | | | | |
|---|---|---|---|---|---|
| Sample timing | | Cell | | | |
| First sample | Sample time X100 us | Area | 1000 mm^2 | Gap | 1000 um |
| 0 | 1 | Gains | | | |
| 20 | 2 | Voltage | 0.7111 kV/V | ○ Small current | 5.0368 uA/V |
| 30 | 5 | Supply factor | 0.309 1/kV | ● Large current | 19.402 uA/V |
| 40 | 10 | | | | |
| 150 | 14 | Display contrast | 12 | | |
| 200 | 20 | Measurement voltage | 1500 V | | |
| 245 | 30 | Voltage threshold 1/ | 4 | | |
| 290 | 45 | Current input clamp | | | |
| 320 | 65 | ○ Unused | | | |
| 350 | 90 | ○ First period count | 2 x100us | | |
| 375 | 135 | ● On threshold | | | |
| 400 | 200 | HF conductivity extrapolation time limits | | | |
| 420 | 300 | Start at 4 ms | End at 8 ms | | |
| 440 | 450 | | | | |
| 455 | 650 | ☐ Download as default values for future use | | | |
| 470 | 900 | This may take few extra seconds | | | |
| 480 | 1350 | | | | |
| 490 | 2000 | Download to instrument | Done | | |
| Measurement time 8206.5 ms | | | | | |

Braces: 72, 74, 76

MEASUREMENT DEVICE AND METHOD THEREOF

BACKGROUND

High field conductivity measurements are typically performed under laboratory conditions. High field conductivity measurements are done in the field with large instruments. High field conductivity is also inferred from measurement of low field conductivity when the substance has low field conductivity.

BRIEF DESCRIPTION OF THE DRAWINGS

Non-limiting examples of the present disclosure are described in the following description, read with reference to the figures attached hereto and do not limit the scope of the claims. In the figures, identical and similar structures, elements or parts thereof that appear in more than one figure are generally labeled with the same or similar references in the figures in which they appear. Dimensions of components and features illustrated in the figures are chosen primarily for convenience and clarity of presentation and are not necessarily to scale. Referring to the attached figures:

DETAILED DESCRIPTION

In the following detailed description, reference is made to the accompanying drawings which form a part hereof, and in which is depicted by way of illustration specific examples in which the present disclosure may be practiced. It is to be understood that other examples may be utilized and structural or logical changes may be made without departing from the scope of the present disclosure. The following detailed description, therefore, is not to be taken in a limiting sense, and the scope of the present disclosure is defined by the appended claims.

In printing presses, such as liquid electrophotography systems, high electric field (herein after "high field") conductivity of ink in particular is inferred from the measurement of the low electric field (hereinafter "low field") conductivity. An example of a low field includes one volt per one hundred microns, and an example of a high field includes one volt per micron. The measurement can be easily done with a device in the press or using a portable instrument. Some ink has a low field conductivity that is low or not measurable. When the low field conductivity is low, the accuracy of the measurements may be compromised. For some inks high field conductivity cannot be inferred from low field data due to their physiochemical structure. To measure conductivity at the high fields directly, large instruments that measure high field conductivity are used to apply a high voltage to the ink to measure the high field conductivity. The large instruments are difficult to carry, require trained personnel to perform the test, and can be disruptive to a process, such as operation of a printing press.

In examples, a measurement device and method to measure a high field conductivity of a fluid are provided. The measurement device includes a fluid cell, a pair of electrodes, a power unit, and a measurement unit. The fluid cell is on an inclined plane to receive the fluid. The pair of electrodes are connected to the fluid cell. The pair of electrodes are spaced apart from one another to receive the fluid therebetween and positioned parallel to one another to pass an electrical current therethrough. The power unit provides a high voltage power supply to one electrode of the pair of electrodes. The measurement unit measures the electrical current that passes between the pair of electrodes through the fluid. The measurement device uses the power unit to apply the high voltage to the ink, which allows the measurement of high field conductivity.

Figure 1:
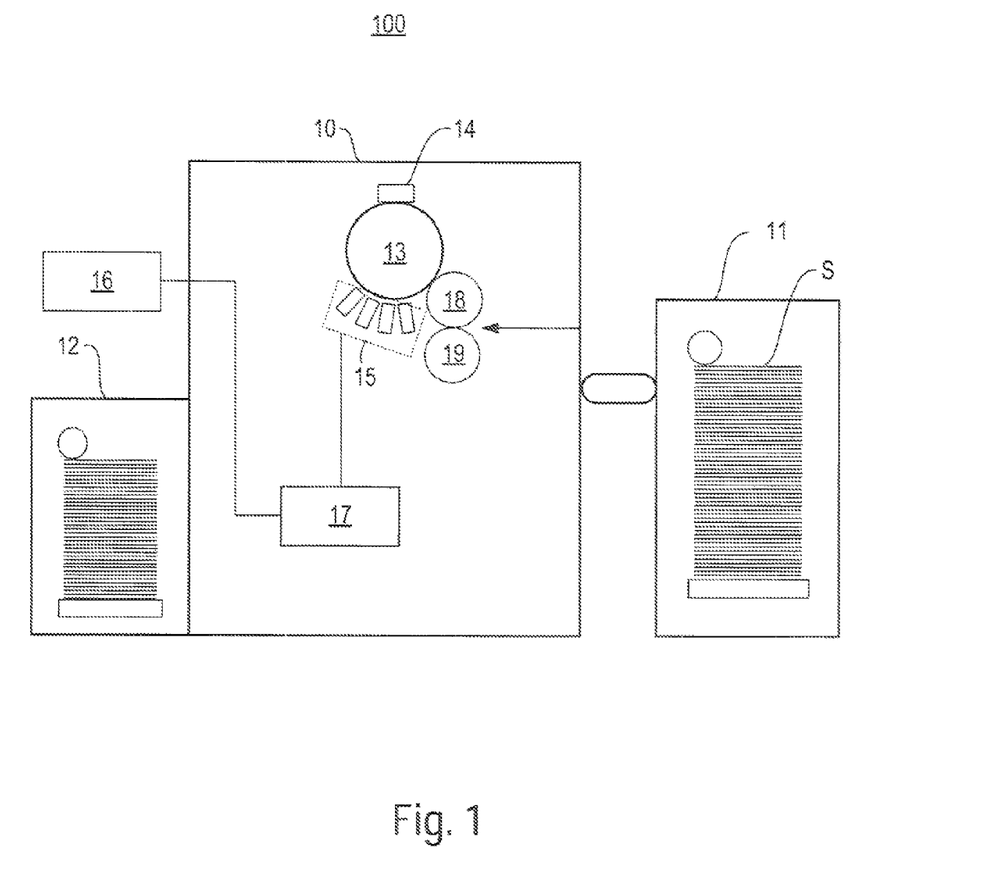
FIG. 1 illustrates a schematic view illustrating an image forming apparatus according to an example.

FIG. 1 illustrates a schematic view illustrating an image forming apparatus, such as a liquid electrophotography system (LEP), according to an example. The LEP 100 includes an image forming unit 10 that receives a media S from an input unit 11 and outputs the media S to an output unit 12. The image forming unit 10 includes a photoconductive member 13 on which images can be formed. The photoconductive member 14 may be charged with a suitable charger (not illustrated), such as a charge roller. Portions of the outer surface of the photoconductive member 13 that correspond to the features of the image can be selectively discharged by a laser writing unit 14 to form an electrostatic and/or latent image thereon.

Referring to FIG. 1, the LEP 100 also includes an applicator unit 15 to apply ink, such as a liquid toner, for example, ElectroInk, trademarked by Hewlett-Packard Company, to the electrostatic and/or latent image on the photoconductive member 13. The ink in the ink applicators is monitored for proper conductivity. A measurement device 16 is used to calibrate the sensors 17 in the press, as the high field conductivity of the ink in the ink applicators affects the quality of the print resulting therefrom. The ink is applied to the photoconductive member 13 to form a fluid image to be transferred to a roller system, including an intermediate transfer member (ITM) 18 and a roller device 19, such as an impression member. The ITM 18 receives the fluid image from the photoconductive member 14, heats the fluid image, and transfers the fluid image to the media S. Heat from the ITM 18 may also transfer to the roller device 19. During the transfer of the fluid image from the ITM 18 to the media S, the media S is pinched between the ITM 18 and the roller device 19. Once the fluid image has been transferred to the media S, the media S can be transported to the output unit 12.

Figure 2:
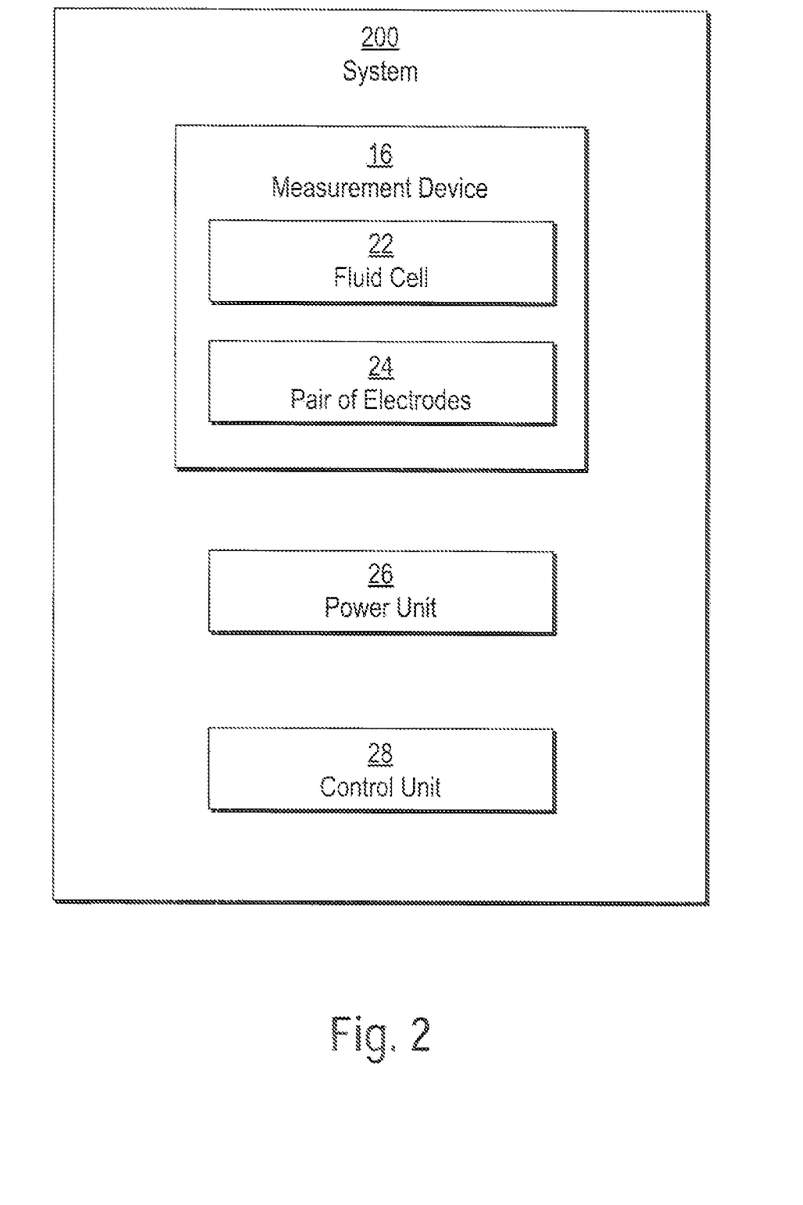
FIG. 2 illustrates a block diagram of a system usable with an image forming apparatus to measure a high field conductivity value according to an example.

FIG. 2 illustrates a block diagram of a system 200 usable with an image forming apparatus to measure a high field conductivity value according to an example. The system 200 includes a measurement device 16 with a fluid cell 22 and a pair of electrodes 24, a power unit 26, and a control unit 28.

Figure 3:
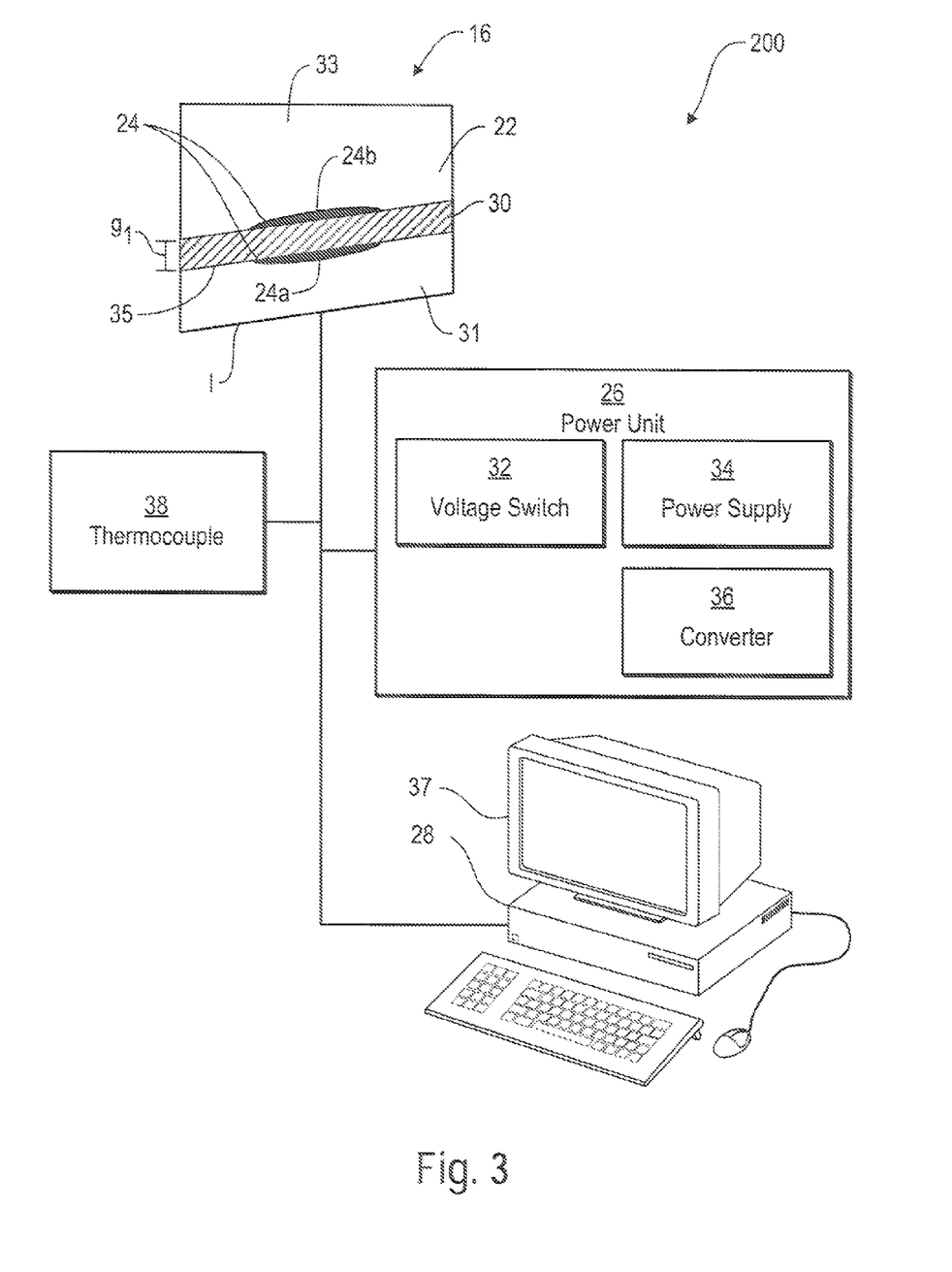
FIG. 3 illustrates a perspective view of the system of FIG. 2 according to an example.

FIG. 3 illustrates a perspective view of the system of FIG. 2 according to an example. The measurement device 16 passes an electrical current through a fluid 30. The measurement device 16 includes a fluid cell 22 and a pair of electrodes 24. The fluid cell 22 is on an inclined plane I with an inclined surface 35. The inclined surface 35 has an upward inclination between, for example, three to five degrees in relation to a horizontal plane. The fluid cell 22 has a base portion 31 and a cover portion 33 opposing the base portion 31.

The pair of electrodes 24 are spaced apart from one another by a distance g1 to allow the fluid 30 therebetween and positioned parallel to one another to pass the electrical current therethrough. The pair of electrodes are also parallel to the inclined plane I. The distance, g1, between the pair of electrodes g1 may be for example one-half a millimeter, one millimeter, and/or three millimeters. The one electrode 24a of the pair of electrodes 24 is connected to the base portion 31, and the other electrode 24b of the pair of electrodes 24 is connected to the cover portion 33.

The power unit 26 includes a voltage switch 32, a power supply 34, and a converter 36. The power supply 34, such as a battery and/or an electrical power supply provides low voltage power to the converter 36. The converter 36 is connected to the voltage switch 32 and the power supply 34. The converter 36 converts low voltage power from the power supply 34 into high voltage power. The power unit 26 passes the high voltage power to the one electrode 24a by, for example, passing the high voltage power from a converter 36 as a high voltage pulse to the one electrode 24a via the voltage switch 32.

The voltage switch 32 controls the transmission of a high voltage pulse from the converter 26 to the one electrode 24a. For example, the voltage switch 32 may be a device that provides the high voltage pulse to the one electrode 24a by turning the high voltage on and off. The voltage switch 32 is rated to switch high voltages, such as up to three kilo volts. Examples of the voltage switch 32 include an electromechanical relay, bipolar junction transistors (BJTs), metal-oxide-semiconductor field-effect-transistors (MOSFETs), insulated gate bipolar transistors (IGBTs), and optocouplers, optorelays, or optoisolators.

The voltage switch 32 typically has a good on-off conduction ratio and must not conduct any current in the off state. The voltage switch 32 may be composed of two voltage switches 32 to counteract a switch that conducts current in the off state. When two switches are used, one is in the off position and the other is in the on position, such that the current that "leaks" from the off switch will go through the on switch. The voltage switch 32 controls rise time of the voltage on the electrode. A short rise time may result in large electromagnetic transients that may be deleterious to operation of the device, while a long a rise time may render measurement meaningless. Typically the rise time may be in the range of twenty to four hundred volts per microsecond. An example of the voltage switch 32 is described below in FIG. 9.

The control unit 28 is connected to the measurement device 16 to obtain the current of the fluid 30 from the other electrode 24b in synchronization with the high voltage pulse. The control unit 28 also calculates the high field conductivity value of the fluid 30 according to the formula:

$$InkConductivity(CellCurrent) := \frac{CellCurrent}{AppliedVoltage} \cdot \frac{CellGap}{ElectrodeArea}.$$

In the formula, CellCurrent is the measured current at a specified time; CellGap is the dimensions of the fluid cell gap g1; AppliedVoltage is the voltage of the pulse applied via the active electrode; and ElectrodeArea is the size of the electrode. The CellCurrent changes over time as apparent conductivity changes with time due to polarization effects. Time dependent conductivity peaks right after voltage is applied before polarization charge builds up in the cell. Typically the peak value is taken as the high field conductivity. Other measurements, such as extrapolation to zero time the region after the peak may also be used.

To perform a measurement, the measurement device 16 receives the fluid 30, moves the fluid 30 along the inclined surface 35, and fills the gap between the pair of electrodes 24 with the fluid 30, such that the fluid covers the pair of electrodes 24. The power unit 26 transmits the high voltage pulse through the fluid 30 via the one electrode 24a. The control unit 28 obtains the electrical current that passes between the pair of electrodes 24 through the fluid 30. The measurement device 16 calculates the high field conductivity value of the fluid 30. The electrical current is obtained in synchronization with the high voltage pulse. The calculation of the high field conductivity value is performed by a processor, such as a microprocessor in the control unit 28. Moreover, the control unit 28 may be a computing device 37, such as a personal computer connected to the measurement device 16. A thermistor or a thermocouple 38 may be connected to the measurement device 16 and/or built into the measurement device 16 to correlate the fluid conductivity with the temperature of the fluid 30. The temperature may also be used by the control unit 28 to calculate a standardized value of the high field conductivity of the fluid 30.

The system 200 may include a user interface including at least one of a graphical user interface, an indicator light, and a control switch. All or a portion of the user interface may be connected to the measurement device 16, such as through a computing device 37 and/or incorporated into the measurement device 16 as illustrated below in FIGS. 5-6. The system 200 may be operated manually using control switches and/or automatically using a computing system that controls the measurement of the high field conductivity.

Figure 4:
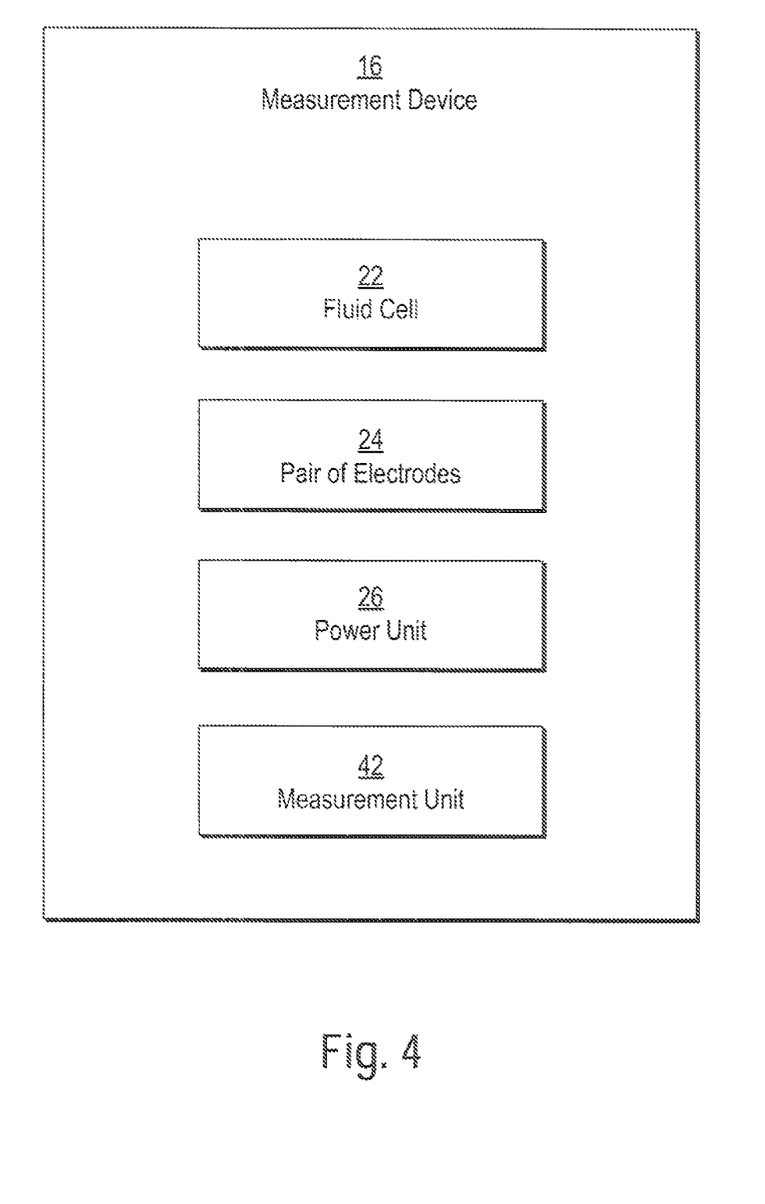
FIG. 4 illustrates a block diagram of a measurement device according to an example.
Figure 5:
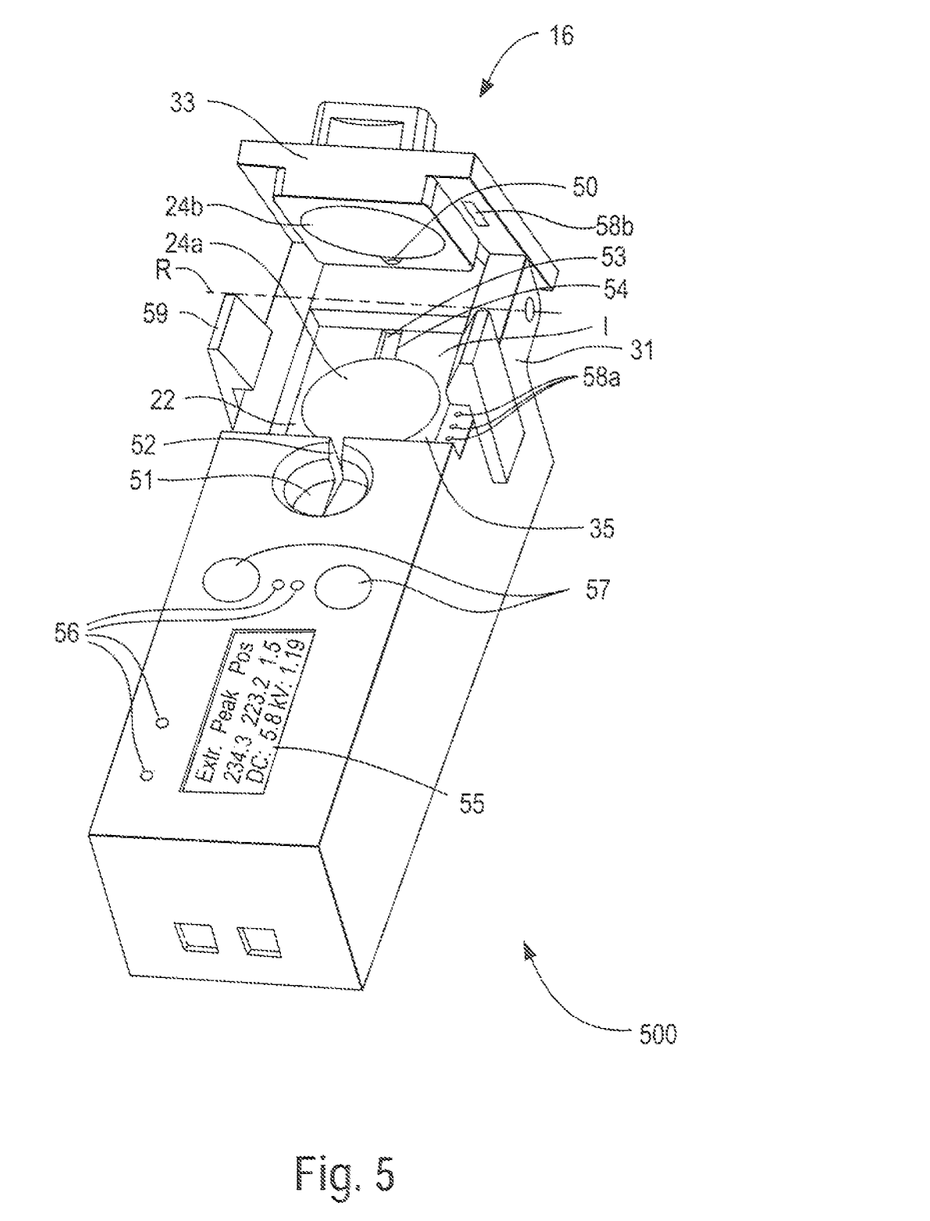
FIG. 5 illustrates a schematic view of the measurement device of FIG. 4 according to an example.
Figure 6:
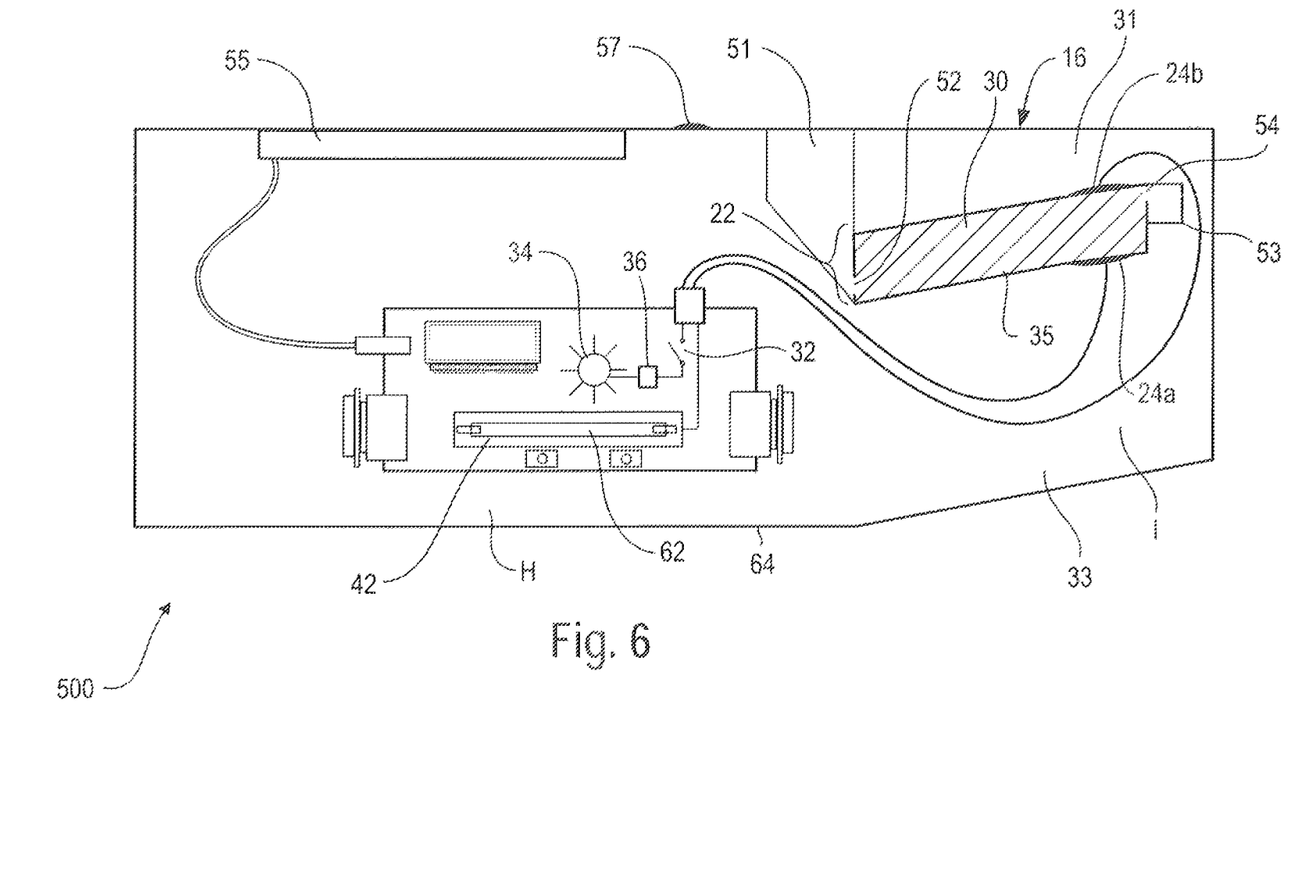
FIG. 6 illustrates a cross-sectional view of the measurement device of FIG. 4 according to an example.

FIG. 4 illustrates a block diagram of a device to measure a high field conductivity value according to an example. The device or measurement device 16 includes a fluid cell 22, a pair of electrodes 24, a voltage switch 34, a converter 36, and a measurement unit 42. Examples of the measurement device 16 are illustrated in FIGS. 5-6. FIG. 5 illustrates a schematic view of the measurement device 16 of FIG. 4 according to an example. FIG. 6 illustrates a cross-sectional view of the measurement device 16 according to an example. The measurement device 16 illustrated in FIGS. 5-6 has the fluid cell 22, pair of electrodes 24, the voltage switch 32, converter 36, and the measurement unit 42 incorporated into one device, such as a handheld device 500.

The fluid cell 22 receives a fluid 30. The fluid cell 22 is on an inclined plane I and has an inclined surface 35. The upward inclination may be between three and five degrees. FIG. 5 illustrates the entire measurement device 16 having an upward inclination.

A fluid reservoir 51 may be connected to the measurement device 16 to fill the fluid cell 22 with the fluid 30. For example the fluid reservoir 51 may be a recessed portion of the measurement device 16 that can receive samples of fluid 30, such as ink, from, for example a pipette. The fluid reservoir 51 may be positioned adjacent to the fluid cell 22 with an inlet aperture 52 therebetween to fill the fluid cell 22. The portion of the fluid cell 22 where the inlet aperture 52 of the fluid reservoir 51 is positioned enables the fluid 30 to enter the fluid cell 22 at or above the lowest point of the inclined surface 35.

The fluid 30 may exit the fluid cell 22 via an overflow reservoir 53. The overflow reservoir 53 may be adjacent to and/or connected to the fluid cell 22 with an outlet aperture 54 therebetween. The overflow reservoir 53 may receive fluid 30 from the fluid cell 22 through an outlet aperture 54 positioned to enable the fluid 30 to exit the cell 22 at or after the highest point of the inclined surface 35. For example, the fluid cell 22 may be filled with excess fluid 30 to push air bubbles out of the fluid cell 22 to improve the accuracy of the electrical current measured. In FIGS. 5-6, the inclined surface 35 facilitates filling the fluid cell 22 without trapping air between the electrodes. The combination of the inclined surface 35 and the ability to release excess fluid 30 after it moves up the inclined surface 35 is a way to reduce the air bubbles in the fluid cell 22. The accuracy of the electrical current measurements improves by avoiding air being trapped between the electrodes 24.

Referring to FIG. 6, the inclined surface 35 extends across a portion of the fluid cell 22 and a level surface 64 extends across a portion of the measurement device 16 adjacent to the fluid cell 22. For example, the level surface 64 may be on a horizontal plane H that intersects the inclined plane I, such that the level surface 64 is approximately parallel to the horizontal plane H. In use, the measurement device 16 may be positioned on the level surface 64 and filled with the fluid 30, which fills from the inclined surface 35 from the bottom toward the top and pushes air bubbles out of the overflow reservoir.

The fluid cell 22 has a pair of electrodes 24 connected thereto. The pair of electrodes 24 are spaced apart from one another by a distance, g1, such as one millimeter to receive the fluid 30 therebetween. The pair of electrodes 24 are positioned parallel to one another to pass an electrical current therethrough. One electrode 24a of the pair of electrodes 24 is illustrated as connected to the base portion 31 of the fluid cell 22 and the other electrode 24b of the pair of electrodes 24 is connected to an opposing surface of the fluid cell 22 on the cover portion 33. For example, the one electrode 24a may be an active electrode connected to the base portion 31 of the fluid cell 22, and the other electrode may be a return electrode connected to the cover portion 33 of the fluid cell 22.

The cover portion 33 may be either fixed or movable, as illustrated in FIGS. 5-6. In either case, the base portion 31 and cover portion 33 position the pair of electrodes 24 parallel to one another to perform the measurement, as the pair of electrodes 24 are positioned parallel to one another to transmit and measure the electrical current. FIG. 6 illustrates the fluid cell 22 in a fixed position with the pair of electrodes 24 positioned parallel to one another. FIG. 5 illustrates the cover portion 33 movable between a position where the pair of electrodes 24 are parallel to one another and are nonparallel to one another. The cover portion's 33 movement may include a rotation around an axis R. For example, the cover portion 33 of FIG. 5 is movable between an open position and a closed position, similar to the fixed position of FIG. 6.

In the closed position an electrical mechanism may form a closed circuit between the cover portion 33 and the fluid cell 22. The electrical mechanism may act like a switch that allows the pulse to pass through the fluid cell 22. The closed circuit is formed when an interlocking bar 58b of the cover portion 33 contacts an electrical connection pin, such as the three electrical connection pins 58a of the fluid cell 22 in the closed position; however, in the open position the interlocking bar 58b is not in contact with the electrical connection pins 58a. To initiate the high voltage pulse at least two of the electrical connection pins 58a are shorted together via the interlock bar 58b. In the closed position, at least one locking tab 59 may also be used to hold and/or secure the cover portion 33 in a position such that the pair of electrodes 24 remain parallel to one another and the base portion 31 and the cover portion 33 forming the fluid cell 22 are in mechanical contact with one another the closed circuit is formed.

The handheld device 500 makes the measurement device 16 portable and improves ease of use. For example, the handheld device 500 illustrated in FIG. 5 may test a sample of the fluid 30, such as an ink, by placing the fluid 30 in the fluid cell 22 via the fluid reservoir 51. A user interface may be on the handheld device 500 to perform the measurement and/or connected to a computing device 37, but in both cases the measurement may be performed easily on site without a laboratory setting. The user interface may include at least one of a graphical user interface 55, an indicator light 56, and a control switch 57. The control switch 57 and indicator light 56 may be used to begin and/or end the measurement and the graphical user interface 55 may provide the measurement results to a user.

FIG. 6 illustrates the electronics of the measurement device 16 including a microprocessor 62, the voltage switch 32, and the measurement unit 42. The electronics may be incorporated into the measurement device 16, as illustrated in FIG. 6 or separate from the measurement device 16, as illustrated in FIG. 3. The voltage switch 32 is connected to the one electrode 24a to provide a high voltage pulse to the one electrode 24a. The voltage switch 32 is illustrated as a switch formed with a plurality of transistors that the high voltage pulse from low voltage direct current (DC) power. For example, the voltage switch 32 may be formed from a relay and off the shelf transistors.

Moreover, the measurement device 16 may be used to test low field conductivity. By adjusting the settings to transmit a low voltage pulse instead of a high voltage pulse, the measurement device 16 may measure low field conductivity. Alternately, a low frequency low amplitude bipolar voltage waveform can be applied under microprocessor 62 control. The resulting current is then measured and correlated with applied waveform voltage to increase signal to noise ratio to measure low field conductivity. The adjustment of settings may be performed with a user interface on the measurement device 16 and/or using a computing device attached thereto. The ability to measure both high and low field conductivity provides one device with versatile functionality for on field testing.

The measurement device 16 also illustrates the measurement unit 42 connected to the other electrode 24b. The measurement unit 42 measures the electrical current of the fluid 30 that passes between the pair of electrodes 24 in synchronization with the high voltage pulse. The measurement unit comprises a microprocessor 62, such as a microprocessor on a breadboard. For example, the measurement unit 42 may be the part of a control unit 28 that measures the electrical current passing through the fluid 30. The microprocessor 62 may have internal analog to digital converters (ADCs) to deal with analog signals, alternatively ADCs may be external to microprocessor 62.

Figure 7:
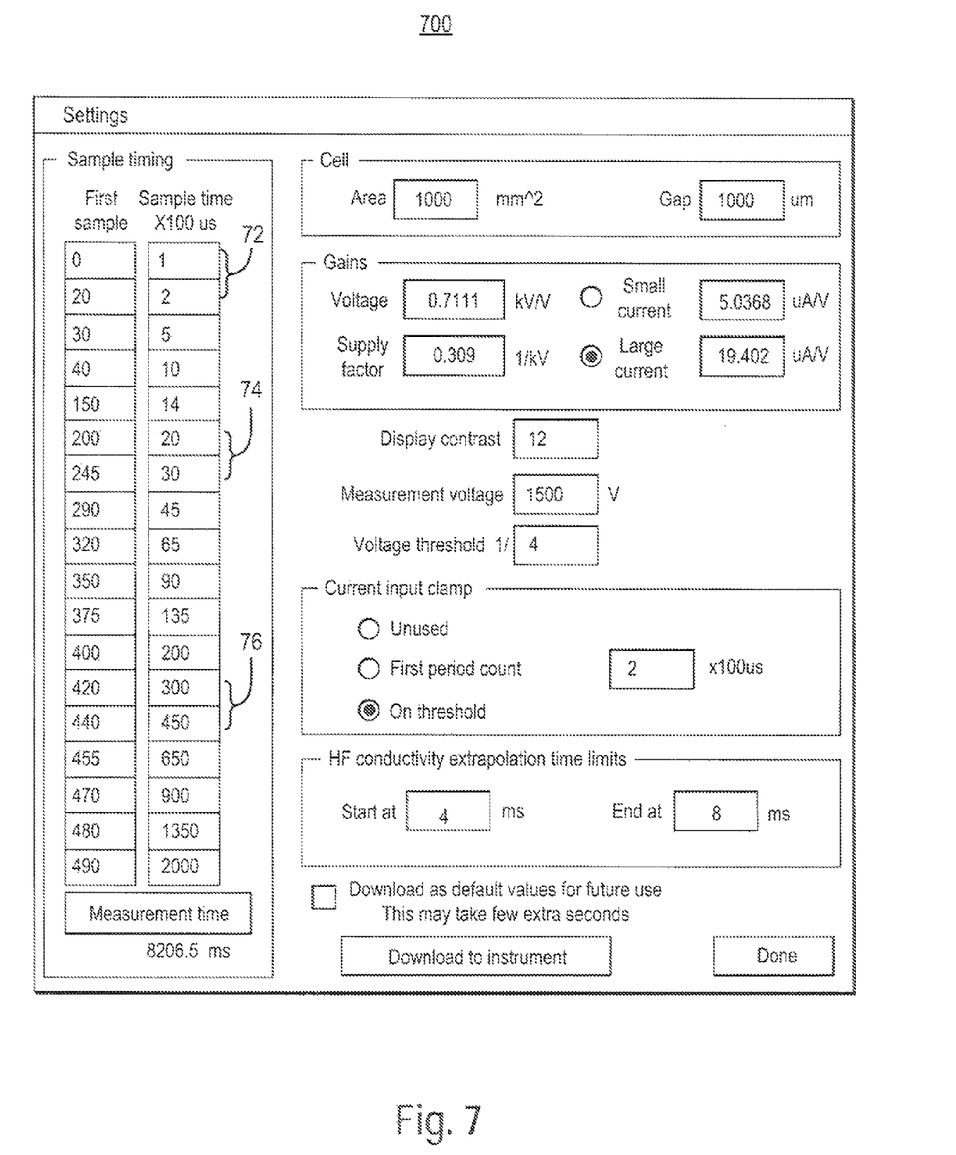
FIG. 7 illustrates data collection settings according to an example.

The measurement unit 42 records the electrical current from the signal electrode at dynamically varying intervals. For example, FIG. 7 illustrates the electrical current recorded in intervals, such as intervals illustrated as dynamically varying between the first sample 72, the two-hundredth sample 74, and/or the four hundred twentieth sample 76. For example, the intervals may be one hundred microseconds per datum between first and twentieth datum 72, intervals of two milliseconds per datum between the two-hundredth sample and the two hundred forty-fifth sample 74, and intervals of thirty milliseconds per datum between the four hundred twentieth sample and the four hundred fortieth sample 76. The first time may be at the beginning of the pulse and the second time may be at the end of the pulse. The data is collected at more frequent time intervals in the beginning of the pulse to minimize data storage and processing without sacrificing accuracy of the measurement. For example, at the beginning of the pulse, or at a first time, the high field conductivity may vary the most and may be obtained either from the peak current or by extrapolating data close to the start of the pulse to pulse start time. The measurement parameters, such as voltage and timing of the data may be set up to default parameters in a manual mode and/or may be changed by an external computer prior to the manual operation and/or in automatic operation.

Figure 8:
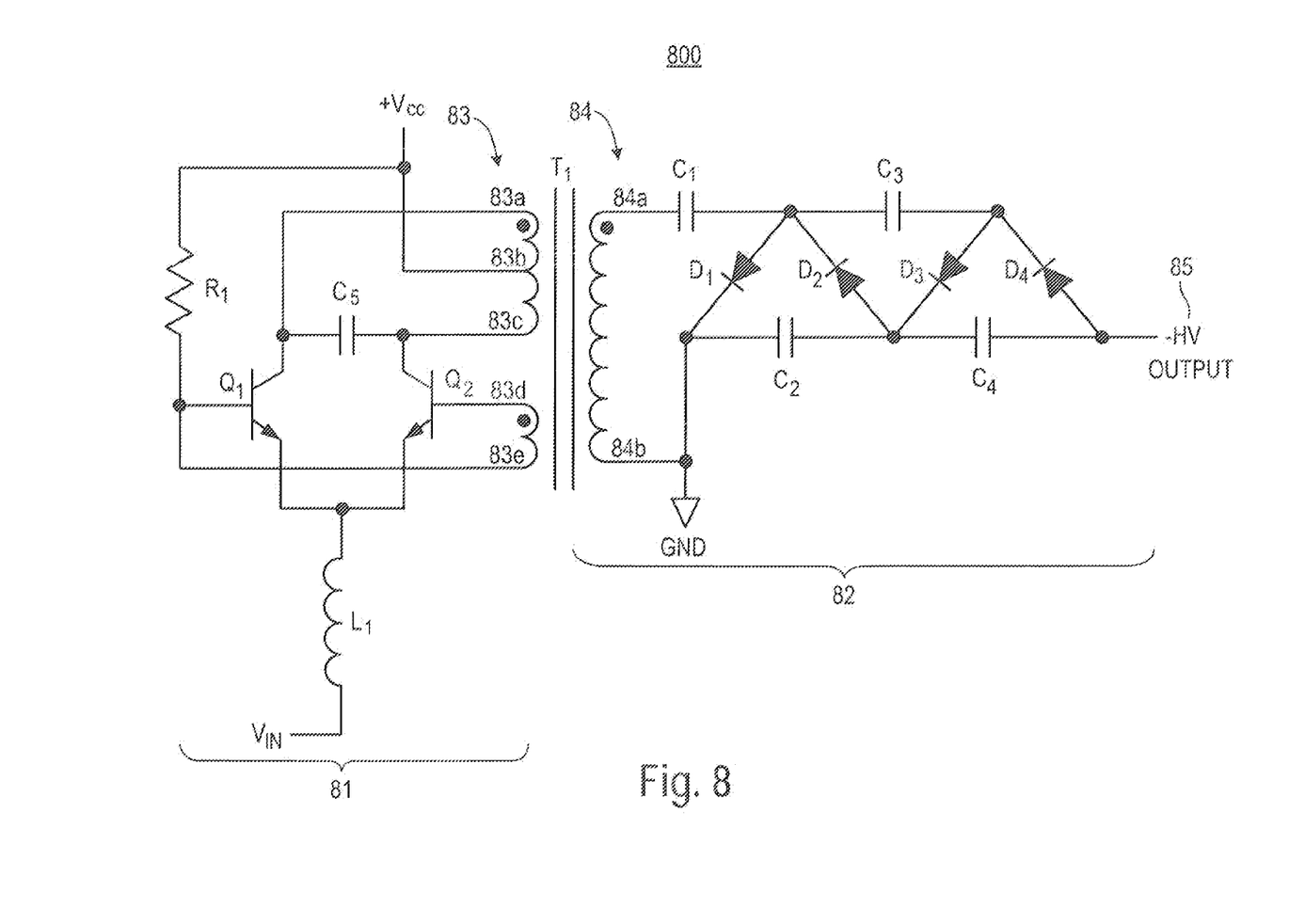
FIG. 8 illustrates a high voltage generator circuit according to an example.

FIG. 8 illustrates a high voltage generator circuit according to an example. Referring to FIG. 8, the converter 36 may be formed from the high voltage generator circuit 800 may generate zero through negative two thousand volts of direct current (VDC), from a low voltage power supply output, such as $V_{CC}$, which is a power supply of positive four and one-half through positive five and one-half VDC, such as a universal serial bus (USB) port connection. The high voltage generator circuit 800 includes an oscillator circuit 81 and its associated cold cathode fluorescent lamp (CCFL) transformer T1, and a diode voltage multiplier circuit 82. The oscillator circuit 81 may be similar to a Royer oscillator circuit. For example, the oscillator circuit 81 is formed by transistors Q1 and Q2, resistor R1, capacitor C5, inductor L1, and the primary side of transformer T1. The Royer oscillator circuit further includes feedback winding pins 83, illustrated as feedback winding pins 83a, 83b, 83c, 83d, and 83e. on the on transformer switch Q1 and the off transformer switch Q2, and vice-versa, at a frequency of approximately fifty kilo Hertz (kHz). The oscillator circuit has a high voltage analog current (AC) output may be rectified and filtered to generate high voltage DC power. The feedback winding pins 83 of the oscillator circuit 81 switch the transistors Q1 and Q2.

The operating frequency in the high voltage generator circuit 800 is determined primarily by capacitors C5 and C1 resonating with the transformer inductance. When the circuit 800 is starting up or the output is heavily loaded, the full value of C1 affects the resonant frequency, in parallel with C5. When the output reaches its steady state value and the output is lightly loaded, there is little current in C1 and it no longer affects the resonant frequency very much. Determining the resonant frequency for C5, and C1 and C5, both in combination with the transformer inductance, is used to verify that the two frequencies are not spread too far apart. For example, if the comparison between C1 and C5 indicates C1 is too large compared, the oscillator circuit 81 transitions to a lower frequency resonance during startup or when heavily loaded, then transitions back up to a higher frequency when the output is more lightly loaded. The transitions make it difficult to control the output voltage.

The CCFL transformer T1 may include a commercially available CCFL transformer with a turns ratio of n=1:100 and primary inductance of twenty micro Henrys (μH), capacitor C1 of one hundred picofarad (pF), and capacitor C5 of one-third microfarad (pF). When lightly loaded C5 has a resonant frequency $f=1/(2 p \cdot \sqrt{(20 \mu H \cdot 0.33 \mu F)})=62$ kHz. When heavily loaded C1 and C5 combined have a resonant frequency $f=1/(2 p \cdot \sqrt{(20 \mu H \cdot (0.33 \mu F+100^2 \cdot 100 pF))})=31$ kHz. For example, the one hundred picofarad capacitor on the secondary side of transformer T1 appears to have $n^2=100^2$ times its capacitance value as seen on the primary side using the calculation $100^2 \cdot 100$ pF=1.00 pF.

The oscillator 81 circuit is fed with a DC input voltage $V_{IN}$, which ranges from $V_{CC}$ down to ground (zero volts). The other power connection to the oscillator circuit 81 is $V_{CC}$. Therefore, the total oscillator input voltage $V_{RO}=(V_{CC}-V_{IN})$, where $V_{CC}$ is less than or equal to $V_{IN}$, which is less than or equal to zero volts. Once the voltage is large enough to start the oscillator (about seven tenths of a volt), the output AC voltage is proportional to input voltage $((V_{cc}-0.7V)-V_{IN})$. For example, the input voltage $V_{IN}$ may be fed through a ballast inductor L1 of about one hundred micro Henrys. The impedance of the ballast inductor L1 may be about thirty-one watts (W) at fifty kilo Hertz, which becomes the emitter load impedance. The resistor, R1 may be two hundred watts. The resistor R1 supplies the base drive current. Together the ballast inductor L1 and the resistor R1 control the oscillator circuit's 81 startup and linearity.

The diode voltage multiplier 82 includes output winding pins 84, illustrated as output winding pins 84a, 84b of transformer T1. The output winding pins 84 provide hundreds of volts AC. The output from the winding pins 84 are fed into a conventional diode voltage multiplier circuit 82 to generate a high voltage DC, in the example case, from zero VDC down to negative two thousand VDC. For example, the capacitors C2, C3, and C4 may be five hundred sixty picofarad rated for three kilo volts, and diodes D1, D2, D3, and D4 are rated for three kilo volts. The proper operation of the oscillator circuit 81 and diode voltage multiplier circuit 82 may be confirmed by measurement.

In order to generate $V_{IN}$ from $V_{CC}$, a conventional pulse width modulation circuit (not shown) may be used. For example, the pulse width modulation circuit may include a MOSFET gate driver that receives a signal from a processor, an N-channel power MOSFET, a Schottky diode, a forty-seven microfarad electrolytic capacitor, and a ten micro Henrys inductor. The pulse width modulation circuit accepts a pulse width modulation (PWM) logic signal from the system processor which is controllable by the processor firmware, such that time t is in seconds and period T is in seconds. In examples, time t is variable and may vary between zero microseconds and two hundred microseconds, and period T is two hundred microseconds. Therefore, given the circuit topology and the duty cycle D=t/T, the output voltage $V_{IN}=(1-D) \cdot V_{CC}$.

The high voltage generated by the high voltage circuit is a clean and low noise high voltage. As illustrated in FIG. 3, the high voltage output is connected to the measurement cell 16. The capacitance of the cell may be about thirty picofarad to conduct AC noise from the high voltage power supply across the cell and into the current measurement input. Currents may be measured down to plus or minus one hundred nanoamperes (nA) or less, with a bandwidth of ten kilo Hertz or more; therefore the AC noise is low. One way to make the AC noise low is to heavily filter the high voltage output –HV to keep the AC noise sufficiently low. Therefore, an output filter may be connected to the high voltage generator circuit between D4 and the high voltage output –HV.

For example, the modified diode voltage multiplier 82 may be directly connected to a ground via one capacitor and a filter section including a resistor and another capacitor connected to a ground. The capacitors are typically six one-hundredths of a microfarad rated for three kilo volts, and the resistor is typically ten kilo Ohms (KΩ). However, the value of resistor may be increased to one hundred kilo Ohms or more, and a rectifier diode or a Zener diode may be added parallel to the resistor. The increased resistance provides more filtering, but increases the voltage drop. The added diode limits the voltage drop, but acts as a high impedance around zero volts or zero load current. For the high voltage generator circuit, a zero load current may be beneficial since the cell current usually tails off to a very small value, such as a microampere or less, and the low cell current is when the high voltage power has the lowest AC noise.

Figure 9:
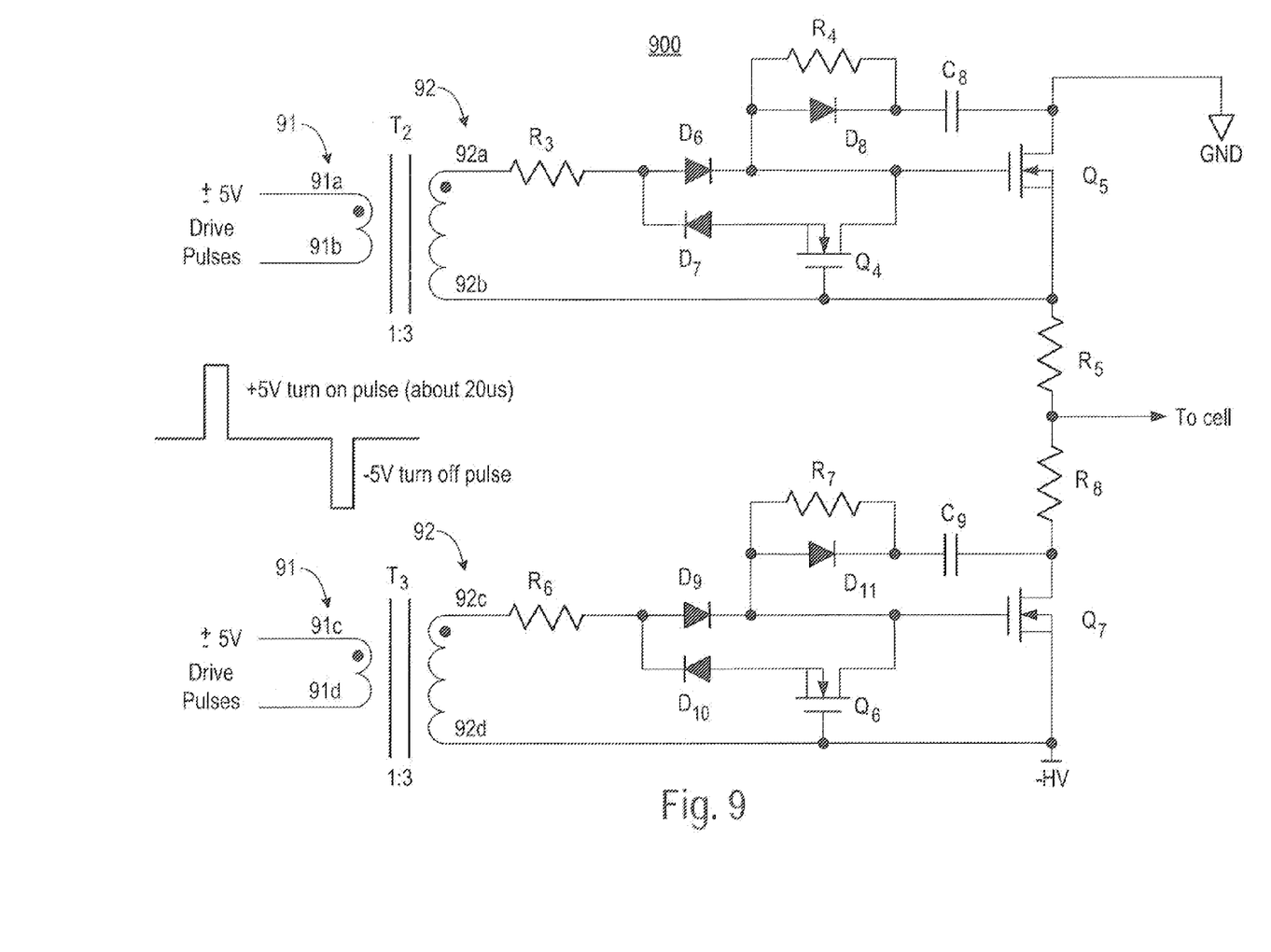
FIG. 9 illustrates a voltage switch according to an example.

FIG. 9 illustrates a voltage switch 32 according to an example. The voltage switch 32 is a solid-state high voltage switch 900, which contains no contact bounce, turns on with a controlled fall time or rise time or slew rate, and has a long lifetime. Referring to FIG. 9, a high voltage power supply, such as the converter 35 described above, provides DC high voltage, such as between negative one thousand VDC to negative two thousand VDC, to the switch 900. The switch 900 connects the fluid cell 22 to ground (zero volts) when the switch 900 is in the off state or to the high voltage when the switch 900 is in the on state. The switch 900 uses either a high voltage Insulated Gate Bipolar Transistors (IGBTs) or Metal-Oxide Semiconductor Field-Effect Transistors (MOSFETs) (Q5, Q7) to switch the high voltage supplied to the fluid cell on and off. The drive circuit for transistors Q5 and Q7 is simply replicated.

Referring to the drive circuit for transformer T3 through transistor Q7. To connect the cell to the DC high voltage, using transistor Q7, the Digital Signal Processor IC (DSP chip) and three and one third volts to negative five volts driver ICs (not shown) provide plus or minus five volt pulses to operate the switch 900. These pulses are isolated from ground and stepped up in voltage by, for example a three to one ratio, by transformer T3. The DSP chip and a driver IC generate a plus or minus five volt pulse for twenty microseconds on the primary winding 91 pins 91c, 91d of transformer T3 (or 91a, 91b of transformer T2), producing a positive fifteen volts for a pulse of twenty microseconds on the secondary winding 92 pins 92d, 92c of transformer T3 (or 92a, 92b of transformer T2). Positive drive current is supplied through resistor R6 and diode D9 to the gate of transistor Q7, causing it to turn on. However, as the drain or collector voltage starts to fall from zero volts down to the negative high voltage DC rail, opposing current starts to flow in diode D11 and capacitor C9. The electrical current (I) is governed by the capacitor current and voltage equation: I=C dV/dt. The drive current and the opposing current quickly reach a balance, which controls the fall time and the slew rate. The values of resistor R6 and capacitor C9 are chosen to control the current magnitudes and the slew rate with a slew of negative two thousand volts in ten microseconds.

Diode D11 ensures that an opposing current is generated only for the turn-on phase. To keep transistor Q7 turned on, positive five volts drive pulses are supplied to transformer T3. The drive waveform cannot have a large DC component. A transformer does not pass DC signals. Diode D9 ensures that only large positive pulses will charge the gate of transistor Q7 and turn it on, even in an AC-coupled waveform, as long as the waveform has low duty cycle. Resistor R8 limits the peak current, in case the test cell is shorted, or both transistors Q5 and Q7 are turned on simultaneously, which avoids damaging the switch 32 or the measurement circuit.

To disconnect the cell from the DC high voltage, the transistor Q7 is turned off. The DSP chip and a driver IC generate a negative five volts pulse for twenty microseconds on the primary winding 91 pins 91c, 91d of transformer T3 (or 91a, 91b of transformer T2), producing a negative fifteen volts for a pulse of twenty microseconds on the secondary winding pins 92c, 92d of transformer T3 (or 91a, 91b of transformer T2). The negative drive current through is supplied through resistor R6, diode D10, and MOSFET Q6 to the gate of transistor Q7, causing it to turn off. Diode D11 ensures that an opposing current is not generated for the turn-off phase. Resistor R7 is typically one hundred Mega ohms which gently and slowly charges capacitor C9 to the steady-state DC voltage across transistor Q7 after it turns off. To keep transistor Q7 turned off, negative five volts drive pulses are applied to transformer T3. The drive waveform cannot have a large DC component. A transformer does not pass DC signals. Diode D10 and MOSFET Q6 ensure that only large negative pulses will discharge the gate of transistor Q7 and turn it off, even in an AC-coupled waveform, as long as the waveform has low duty cycle.

The operation of the switch 900 depends upon the ability to turn transistor Q5 and Q7 on or off based upon how much charge is stored in its gate electrode. The gates of both MOSFETs and IGBTs behave like capacitors. If enough charge is stored on the gate, the transistor turns on. Removing all the charge turns the transistor off. Leaving the charge in place leaves the transistor in the same state; hence, the gate drive current is pulsed occasionally to keep the transistor on or off.

Figure 10:
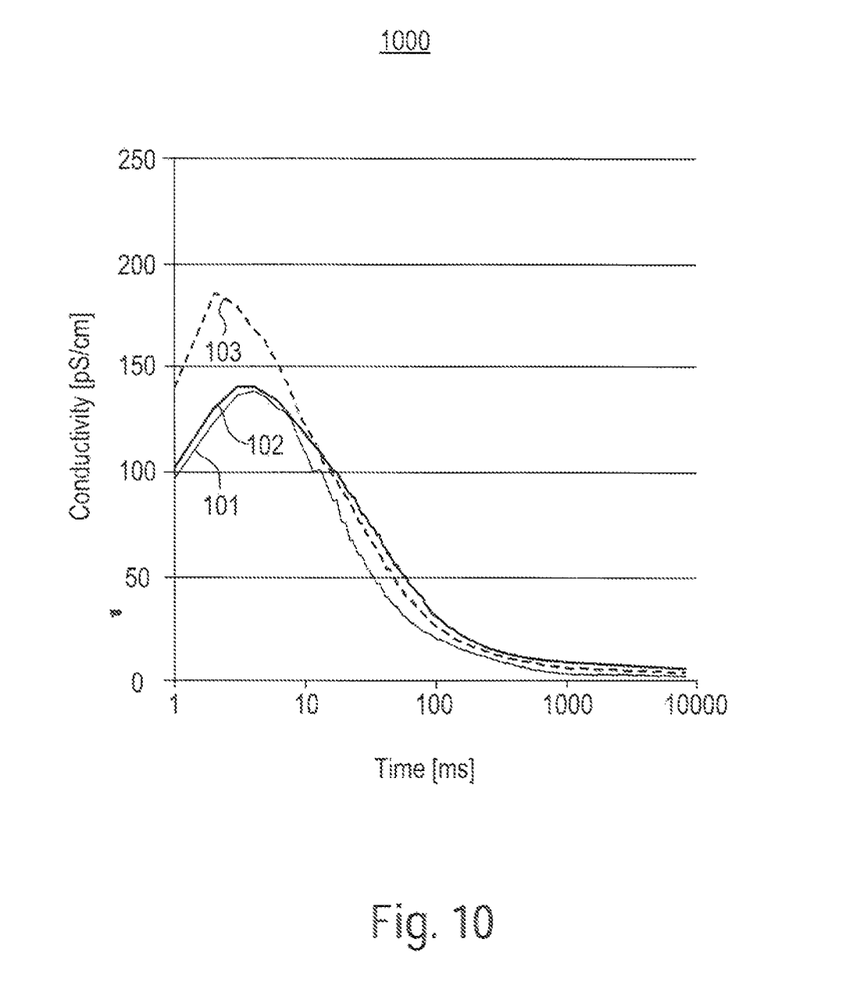
FIG. 10 illustrates a graphical depiction of high field conductivity values of magenta ink according to an example.

FIG. 10 illustrates a graphical depiction 1000 of high field conductivity values of magenta ink according to an example. The gap between the pair of electrodes 24 used for the measurement was one millimeter except for curve 102 where one half a millimeter was used. As illustrated, the conductivity value peaks at the beginning of a pulse, i.e. during the first ten milliseconds and decreases between ten and one thousand milliseconds, where the conductivity leveled off through ten thousand milliseconds. The graph illustrates measurements of conductivity in picoSiemens per centimeter (pS/cm), for example, two measurements are illustrated at six tenths of a kilo volt 101, 102 and one measurement is illustrated at nine tenths of a kilo volt 103. The measurements at six tenths of a kilo volt 101, 102 and at nine tenths of a kilo volt 103 illustrate similar conductivity patterns, but point out large field dependence. As curves 102 and 101 illustrate the peak conductivity does not depend significantly on the cell thickness, but overall time dependence does, as polarization effects are affected by electrode spacing.

Figure 11:
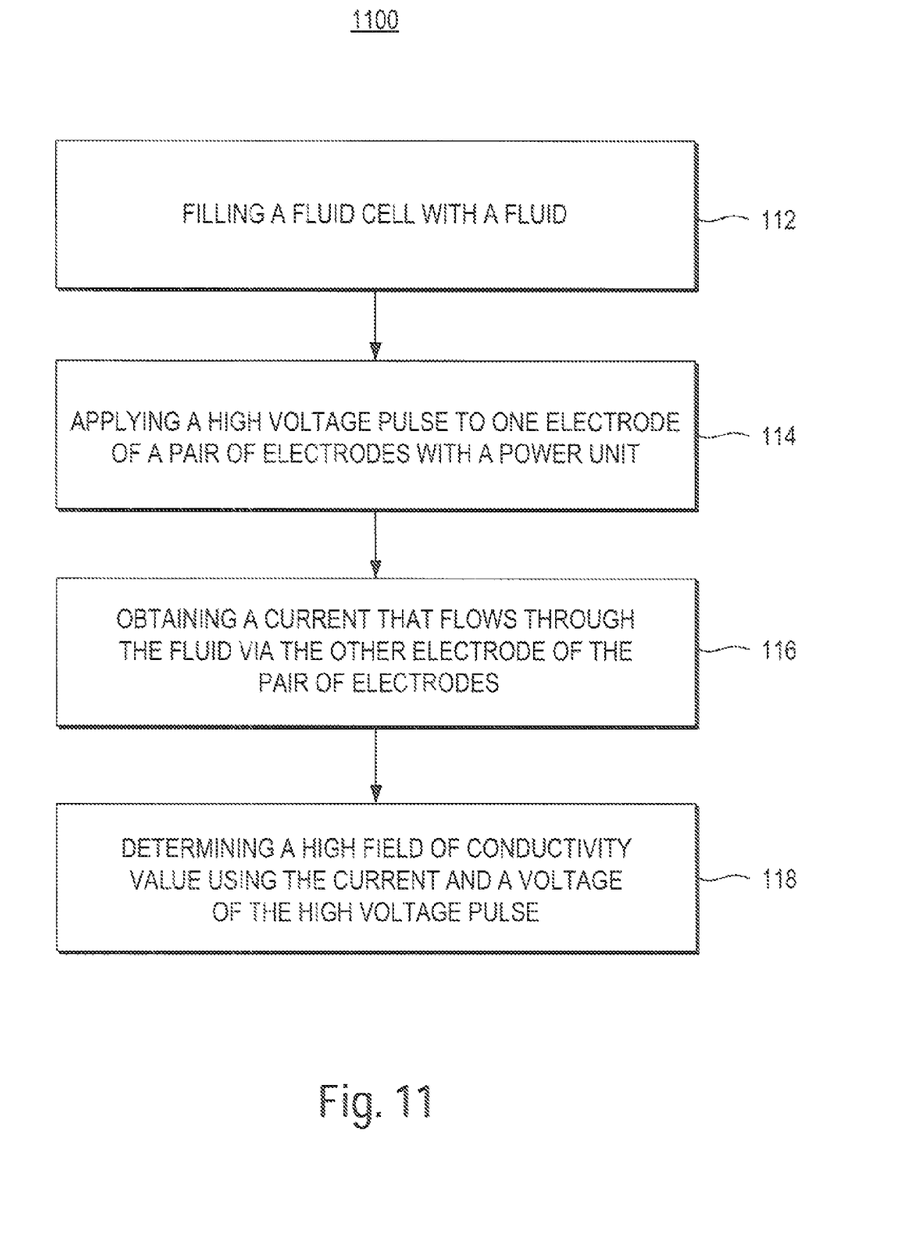
FIG. 11 illustrates a flowchart of a method of measuring a high field conductivity value according to an example.

FIG. 11 is a flowchart illustrating a method 1100 of measuring a high field conductivity value according to an example. In block 112, a fluid cell is filled with fluid. The fluid cell lies in an inclined plane. During filling fluid moves upward along the inclined plane. The fluid in the fluid cell covers a pair of electrodes spaced apart from one another and positioned parallel to one another. A high voltage pulse is applied to one electrode of the pair of electrodes with a power unit in block 114. The power unit includes a converter to convert a low voltage power supply to the high voltage power supply and a voltage switch to control the high voltage pulse. An electrical current that passes between the pair of electrodes through the fluid is obtained in block 116 from the other electrode of the pair of electrodes. The electrical current measurement is synchronized with the high voltage pulse, such that the electrical current may be recorded at dynamically varying intervals, for example intervals of one hundred microseconds per datum at a first time and intervals of one hundred milliseconds per datum at a second time, as illustrated in FIG. 7. By recording the current at dynamically varying intervals, the data collected is targeted to specific times during the high voltage pulse. By targeting the specific times during the high voltage pulse, fewer data points may be collected, while accurately recording and/or charting the high field conductivity, as illustrated above in FIG. 7. Typically a low field conductivity measurement would precede high field measurement if the measurement device has that capability.

In block 118, the high field conductivity value is determined using the electrical current and a voltage of the high voltage pulse corresponding thereto. The high field conductivity value is determined with a microprocessor. The method 1100 may also correlate the conductivity of the fluid to the temperature of the fluid. The method 1100 may also use the temperature of the fluid to determine a standardized high field conductivity value. The high voltage pulse may be controlled with a computing device. The high field conductivity value is displayed on a user interface, such as an interface on the measurement device and/or on a computing device.

The method 1100 further includes measuring a low field conductivity value. For example, the low field conductivity value may be measured prior to applying the low voltage waveform. The low field conductivity value is measured with the microprocessor. A voltage switch applies the low voltage waveform, as a low voltage pulse to the one electrode of the pair of electrodes. The other electrode obtains the pair of electrodes the electrical current that flows through the fluid between the pair of electrodes in synchronization with the low voltage pulse. The microprocessor determines the low field conductivity value using the electrical current and the voltage of the low voltage waveform corresponding thereto. Alternatively a low frequency, such as ten Hertz, low alternating voltage pulse is applied by microprocessor to the cell and conductivity is determined from current flowing in response to the alternating voltage. Using the alternating voltage helps increase measurement sensitivity by Fourier transform filtering the electrical current data which increases signal to noise.

For example, the voltage switch may not be the same switch that provides the high voltage pulse, but may be in the path of the low voltage signal being applied to the electrode. The converter that provides the high voltage pulse is electrically floated. During the high voltage measurement, the converter's floating ground is at the voltage of actual ground. When high voltage is not applied, the one electrode is connected to the floating ground of the converter. For measurement of the low field conductivity value, the low voltage waveform is applied to the floating ground which in effect transfers it to the one electrode.

The present disclosure has been described using non-limiting detailed descriptions of examples thereof and is not intended to limit the scope of the present disclosure. It should be understood that features and/or operations described with respect to one example may be used with other examples and that not all examples of the present disclosure have all of the features and/or operations illustrated in a particular figure or described with respect to one of the examples. Variations of examples described will occur to persons of the art. Furthermore, the terms "comprise," "include," "have" and their conjugates, shall mean, when used in the present disclosure and/or claims, "including but not necessarily limited to."

It is noted that some of the above described examples may include structure, acts or details of structures and acts that may not be essential to the present disclosure and are intended to be exemplary. Structure and acts described herein are replaceable by equivalents, which perform the same function, even if the structure or acts are different, as known in the art. Therefore, the scope of the present disclosure is limited only by the elements and limitations as used in the claims.

What is claimed is:

1. A device to measure a high field conductivity value, the device comprising:
   a housing comprising a horizontal level surface to rest upon an underlying horizontal supporting surface so as to support the device;
   a fluid cell on an inclined plane to receive a fluid, the inclined plane to receive the fluid and having an upwardly facing inclined surface with an upward inclination along the inclined plane, the inclined surface deviating with respect to both a horizontal and a vertical when the horizontal level surface is resting upon the underlying horizontal supporting surface;
   a pair of electrodes connected to the fluid cell, the pair of electrodes spaced apart from one another to receive the fluid therebetween and positioned parallel to one another to pass an electrical current therethrough;
   a power unit connected to one electrode of the pair of electrodes to provide a high voltage pulse to the one electrode, the power unit including a converter to convert a low voltage power supply to the high voltage power supply and a voltage switch to control the high voltage pulse; and
   a measurement unit connected to the other electrode of the pair of electrodes to measure the electrical current that passes between the pair of electrodes through the fluid in synchronization with the high voltage pulse.

2. The device of claim 1, wherein the measurement unit records the electrical current from the other electrode at dynamically varying intervals.

3. The device of claim 1 wherein the voltage switch controls the rise time of the high voltage pulse.

4. The device of claim 1, wherein the fluid cell further comprises
   a base portion having the inclined surface formed thereon; and
   a cover portion extending over and opposing the base portion.

5. A measuring system usable with an image forming device, the measuring system comprising:
   a measurement device to pass an electrical current through a fluid, the measurement device including:
      a housing having an underlying horizontal level surface to rest upon an underlying horizontal supporting surface so as to support the measurement device;
      a fluid cell having:
         a base portion comprising an upwardly facing floor on top of which fluid is received, the floor having a lower portion and an upper portion vertically above the lower portion when the horizontal level surface is resting upon the underlying horizontal supporting surface, and
         a cover portion opposing and extending over the floor of the base portion, and
      a pair of electrodes, the pair of electrodes spaced apart from one another to allow the fluid therebetween and positioned parallel to one another to pass the electrical current therethrough, one electrode of the pair of electrodes connected to the base portion, and the other electrode of the pair of electrodes connected to the cover portion;
   a power unit to provide a high voltage pulse to the one electrode, the power unit having a converter to convert a low voltage power supply to a high voltage power supply and a voltage switch to control the high voltage pulse; and
   a control unit connected to the measurement device to:
      obtain the electrical current that passes between the pair of electrodes through the electrodes in synchronization with the high voltage pulse, and
      calculate the high field conductivity value of the fluid using the electrical current,
      wherein the measurement device receives the fluid, moves the fluid along the floor, and covers the pair of electrodes with the fluid, the power unit transmits the high voltages pulse through the fluid via the one electrode, and the control unit obtains the electrical current that passes through the fluid via the other electrode and calculates the high field conductivity value of the fluid.

6. The system of claim 5, further comprising:
a fluid reservoir having an outlet connected to the floor of the measurement device to fill the fluid cell with the fluid; and
an overflow reservoir having an inlet connected to the floor of the measurement device to receive the fluid that exits the fluid cell, the inlet being vertically above the outlet when the horizontal level surface is resting upon the horizontal supporting surface.

7. The system of claim 5 wherein the voltage switch controls the rise time of the high voltage pulse.

8. The system of claim 5, further comprising a thermocouple to measure a temperature of the fluid.

9. The system of claim 5, wherein the measuring device determines a low conductivity value, the measuring device to:
apply a low voltage waveform to the one electrode of the pair of electrodes;
obtain from the other electrode of the pair of electrodes the electrical current that flows through the fluid between the pair of electrodes in synchronization with the low voltage waveform; and
determine the low field conductivity value using the electrical current and the voltage of the low voltage waveform corresponding thereto.

10. A method of measuring a high field conductivity value, the method comprising:
filling a fluid cell with a fluid, the fluid cell having an inclined plane with an upwardly facing inclined surface that moves the fluid along an upward inclination, such that the fluid covers a pair electrodes spaced apart from one another and positioned parallel to one another, the inclined surface deviating with respect to both a horizontal and a vertical;
applying a high voltage pulse to one electrode of the pair of electrodes with a power unit including a converter and a voltage switch;
obtaining from the other electrode of the pair of electrodes an electrical current that passes between the pair of electrodes through the fluid in synchronization with the high voltage pulse; and
determining with a microprocessor the high field conductivity value using the electrical current and a voltage of the high voltage pulse corresponding thereto.

11. The device of claim 4, wherein the cover portion is movable between an open position and a closed position.

12. The system of claim 5, wherein the cover portion is movable between an open position and a closed position.

13. The system of claim 12, wherein the cover portion pivots between the open position and the closed position.

14. The system of claim 13, wherein the cover portion carries one electrode of the pair of electrodes.

15. The system of claim 12, wherein the cover portion in the closed position closes an electrical circuit allowing the pair of electrodes to provide an electrical pulse to the fluid cell and in the open position opens the electrical circuit inhibiting the pair of electrodes from providing the electrical pulse to the fluid cell.

16. The system of claim 12, wherein the pair of electrodes are parallel when the cover portion is in the closed position.

17. The system of claim 5, wherein the floor linearly extends from the lower portion to the upper portion.

18. The device of claim 1 further comprising:
a fluid reservoir having an outlet connected to the inclined surface of the measurement device to fill the fluid cell with the fluid; and
an overflow reservoir having an inlet connected to the inclined surface of the measurement device to receive the fluid that exits the fluid cell, the inlet being vertically above the outlet when the horizontal level surface is resting upon the horizontal supporting surface.

19. The device of claim 1, wherein the inclined surface extends oblique to the underlying horizontal supporting surface.

20. The method of claim 10, wherein the fluid cell is provided within a housing having a horizontal level surface to rest upon an underlying horizontal supporting surface and wherein the method further comprises resting the horizontal level surface upon the underlying horizontal supporting surface while the fluid moves along the inclined surface and the upward inclination.

* * * * *